United States Patent
Xie et al.

(10) Patent No.: US 8,029,743 B2
(45) Date of Patent: Oct. 4, 2011

(54) MICROFLUIDIC DEVICE WITH VERTICAL INJECTION APERTURE

(75) Inventors: Jun Xie, Niskayuna, NY (US); Shashi Thutupalli, Bangalore (IN); Stacey Joy Kennerly, Albany, NY (US); Wei-Cheng Tian, Clifton Park, NY (US); Erin Jean Finehout, Clifton Park, NY (US); Li Zhu, Clifton Park, NY (US); Oliver Charles Boomhower, Waterford, NY (US)

(73) Assignee: General Electric Company, Niskayuna, NY (US)

( * ) Notice: Subject to any disclaimer, the term of this patent is extended or adjusted under 35 U.S.C. 154(b) by 988 days.

(21) Appl. No.: 11/857,570

(22) Filed: Sep. 19, 2007

(65) Prior Publication Data

US 2009/0071832 A1    Mar. 19, 2009

(51) Int. Cl.
    *B01L 3/00*    (2006.01)
    *G01N 27/453*  (2006.01)
(52) U.S. Cl. ...................... 422/503; 204/604
(58) Field of Classification Search .......... 204/601–605, 204/451–455; 422/99, 100, 503
    See application file for complete search history.

(56) References Cited

U.S. PATENT DOCUMENTS

| | | | |
|---|---|---|---|
| 4,879,247 A | 11/1989 | Ohlson | |
| 5,171,563 A | 12/1992 | Abrams et al. | |
| 5,644,395 A | 7/1997 | Folta | |
| 5,976,336 A * | 11/1999 | Dubrow et al. | 204/453 |
| 6,190,521 B1 * | 2/2001 | Virtanen | 204/453 |
| 6,251,343 B1 | 6/2001 | Dubrow et al. | |
| 6,953,567 B2 | 10/2005 | Griffiths | |
| 7,211,240 B2 | 5/2007 | Arbogast et al. | |
| 7,294,247 B1 * | 11/2007 | Tian et al. | 204/451 |
| 2002/0197736 A1 | 12/2002 | Amirkhanian | |
| 2005/0150766 A1 | 7/2005 | Manz et al. | |

FOREIGN PATENT DOCUMENTS

| | | |
|---|---|---|
| EP | 0268406 A2 | 11/1987 |
| JP | 05-072178 A * | 3/1993 |
| WO | 9604547 A1 | 2/1996 |
| WO | 9934220 A2 | 7/1999 |

OTHER PUBLICATIONS

JPO computer-generated English language translation of Kanbara JP 05-072178 A.*
P.F. Man et al., "Microfluidic Plastic Capillaries on Silicon Substrates: A New Inexpensive Technology for Bioanalysis Chips," Center for Integrated Sensors and Circuits, IEEE, 48109-2122, 0-7803-3744-1, 1997, pp. 311-316.
P.Y. Chiou et al., "Massively parallel manipulation of single cells and microparticles using optical images," Nature, vol. 436, Jul. 2005, pp. 370-372.

* cited by examiner

*Primary Examiner* — Alex Noguerola
(74) *Attorney, Agent, or Firm* — Jenifer E. Haeckl

(57) ABSTRACT

A microfluidic device with a vertical injection aperture is provided. The microfluidic device comprises a separation channel, an injection aperture disposed adjacent to and in fluid communication with the separation channel. The microfluidic device further comprises a semi-permeable filter disposed adjacent to the injection aperture, wherein the filter is configured to preconcentrate a sample in the injection aperture to form a preconcentrated sample plug during an injection operation, and wherein the sample plug flows downwardly from the injection aperture to the separation channel during an electrophoresis operation.

6 Claims, 8 Drawing Sheets

MICROFLUIDIC DEVICE WITH VERTICAL INJECTION APERTURE

BACKGROUND

The invention relates generally to microfluidic devices and more particularly to a system and method for sample injection onto a microfluidic capillary electrophoresis channel.

Electrophoretic separation of bio-molecules is very important in modern biology and biotechnology applications such as DNA sequencing, protein molecular weight determination and genetic mapping. Electrophoresis is a process by which individual molecular species are separated in a conductive medium (such as a liquid solution or a cross-linked polymer) by applying an electric field. The charged molecules migrate through the solution and separate into distinct bands due to their mobility difference through the media. The rates are influenced by factors such as a viscosity of the solution, a mass and charge of the molecules, and a strength and duration of the electric field.

An increase in a voltage gradient (V/cm) applied to the electrophoretic device results in a corresponding decrease in the time needed to perform the separation. However, increasing the voltage gradient is governed by certain constraints. For example, increasing the voltage gradient beyond a certain point may result in an increase in joule heating which would in turn alter the properties of the medium in which the molecules are being separated. The change of the medium properties leads to an increase in sample diffusion and thus degraded the separation resolution. In order to overcome the above limitations, electrophoresis can be performed in a capillary or miniaturized channel. The large surface-area-to-volume ratio of the electrophoretic devices offers efficient dissipation of Joule heat, allowing higher electric field to be used, thus resulting in the shorter analysis time and better separation efficiency.

Microfluidic devices are small compact devices that perform chemical and physical operations such as capillary electrophoresis with microscale sample volumes. These devices often have the benefits of fast reactions, rapid detection, small reagent consumption, ease of automation and simple transfer between reaction vessels. Microfluidic devices are commonly referred to as "lab-on-a-chip."

Typically in microfluidic devices, sample volumes used are very low, thus making it difficult to detect analytes of low concentration. Often, a "preconcentration" step is incorporated into the microfluidic device to increase the sample analyte concentration. However, the typical concentration techniques are not applicable to microfluidic devices due to the small sample size capacity of the device. In addition, concentrating the analyte of interest may also lead to contaminating the analytes, which can interfere with the downstream analysis. For example, in electrokinetic injection, a high concentration of contaminating salt ions will decrease the amount of the charged analyte that is loaded onto the analysis channel.

In field-amplified sample stacking, the sample is dissolved in a low ionic conductivity solution, which in turn contacts a high ionic conductivity solution in the channel, and an electric field causes the sample salts (or ions) to flow into the high ionic conductivity solution, thereby increasing the sample analyte concentration in the low ionic conductivity solution. However, the sample preconcentration may still be insufficient for high optical detection sensitivity.

In filtered sample stacking, the sample flows into a filter such as a porous polymer plug with a pore size that allows small molecules to pass through but blocks larger molecules (such as proteins or DNA). The sample is preconcentrated upstream of the filter. However, the filter is often formed in the channel using complex and cumbersome manufacturing techniques. Furthermore, the filter is permanently attached to the channel, and therefore the microfluidic device must be discarded if the filter clogs, tears or otherwise deteriorates.

Therefore, there is a need for a microfluidic device that provides sample preconcentration, minimizes the effect of concentrating small molecule contaminants, and reproducibly loads a small sample volume onto an analysis channel in a convenient and cost-effective manner.

BRIEF DESCRIPTION

According to one embodiment of the invention, a microfluidic device is provided. The microfluidic device comprises a separation channel, an injection aperture disposed adjacent to and in fluid communication with the separation channel. The microfluidic device further comprises a semi-permeable filter disposed adjacent to the injection aperture, wherein the filter is configured to preconcentrate a sample in the injection aperture to form a preconcentrated sample plug during an injection operation, and wherein the sample plug flows downwardly from the injection aperture to the separation channel during an electrophoresis operation.

In another embodiment, a microfluidic device is provided. The microfluidic device comprises a separation channel comprising a detection zone. The detection zone is disposed downstream of an injection aperture and upstream of a waste aperture. The microfluidic device further comprises a semi-permeable filter disposed adjacent to and covering the injection aperture, and configured to preconcentrate and desalt a sample to form a preconcentrated sample plug in the injection aperture during an injection operation. The sample flows downwardly from a sample well through a sample aperture to the separation channel, flows longitudinally in the separation channel from the sample aperture to the injection aperture and flows upwardly in the injection aperture to the filter. The sample plug flows downwardly from the injection aperture to the separation channel and flows longitudinally in the separation channel from the injection aperture to the detection zone during an electrophoresis operation.

In another embodiment, a microfluidic device is provided. The microfluidic device comprises a bottom plate comprising a separation channel, a top plate comprising a sample aperture, an injection aperture and a waste aperture. The sample aperture, the injection aperture and the waste aperture are in fluid communication with the separation channel. The microfluidic device further comprises a well plate comprising a sample well, a buffer well and a waste well and a semi-permeable filter disposed between the injection aperture and the buffer well.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
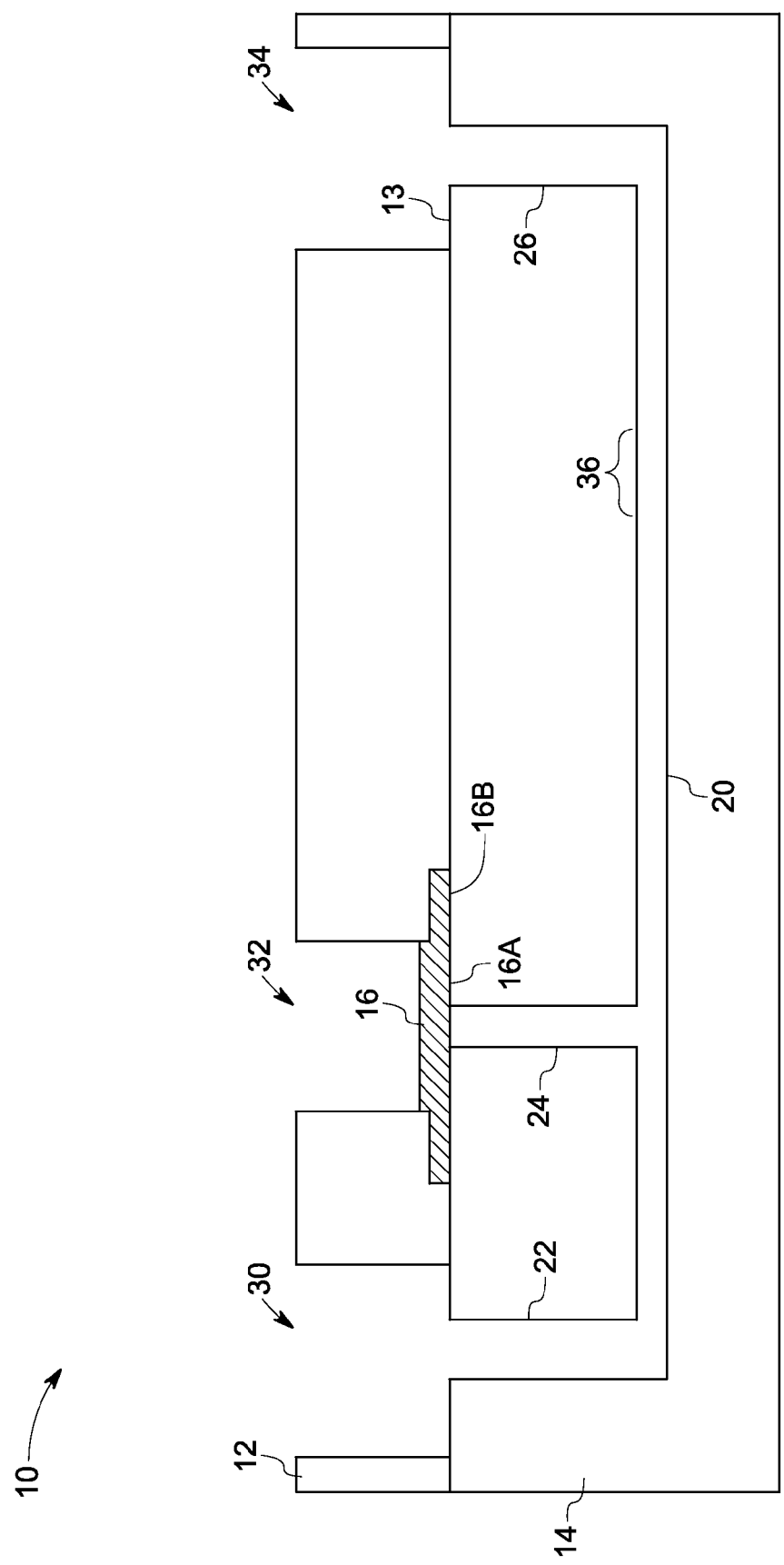
FIG. 1 is a sectional view of an embodiment of a microfluidic device implemented according to one aspect of the invention.
Figure 2:
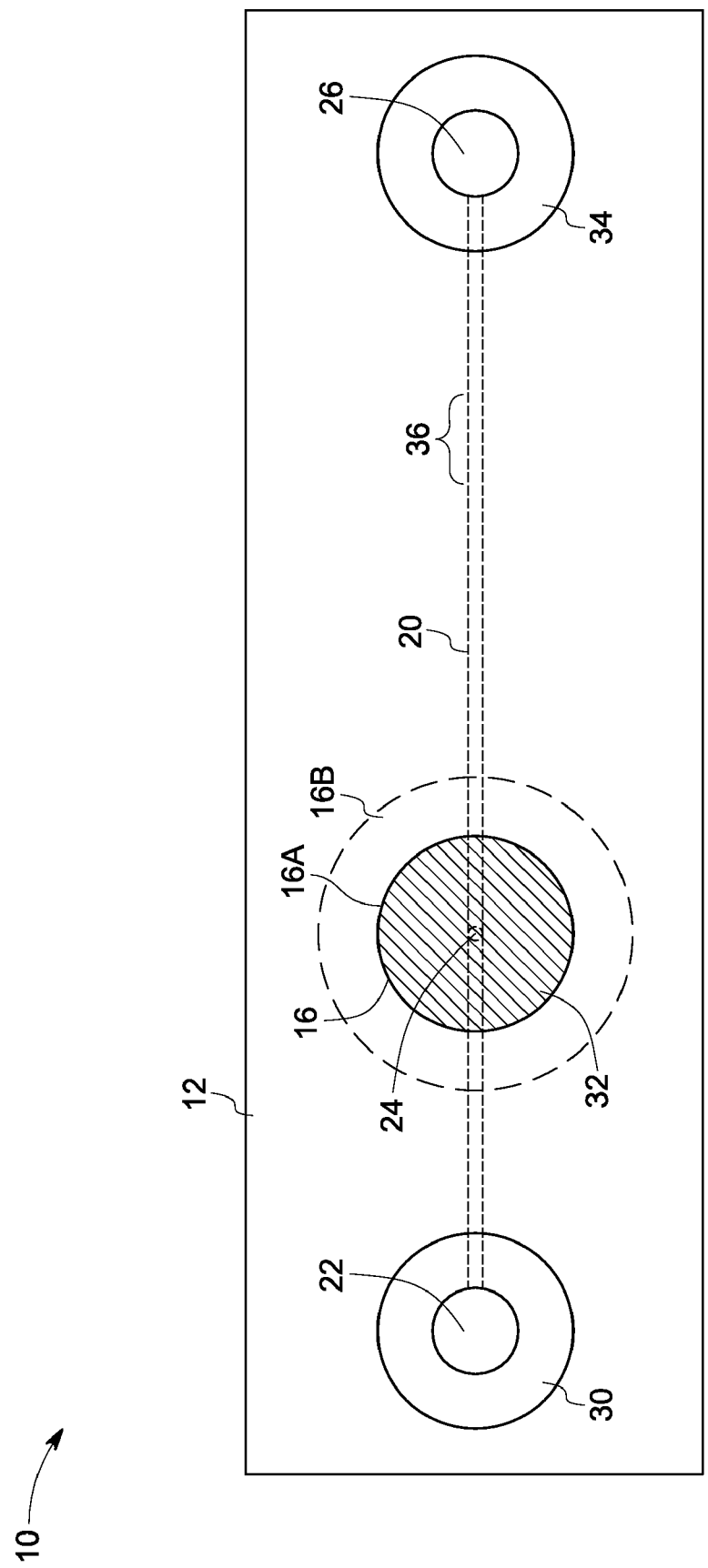
FIG. 2 is a top view of the microfluidic device illustrated in FIG. 1.

FIG. 1 is a sectional view of an embodiment of a microfluidic device implemented according to one aspect of the invention. FIG. 2 is a top view of the microfluidic device shown in FIG. 1. The microfluidic device is described with reference to a capillary electrophoresis channel. However, it may be noted that the device and method described below can be implemented on other types of analysis channels as well. Microfluidic device 10 comprises bottom plate 14, top plate 13, well plate 12 and filter 16. Each component is described in further detail below.

Bottom plate 14 includes separation channel 20 and top plate 13 includes sample aperture 22, injection aperture 24 and waste aperture 26. Separation channel 20 includes detection zone 36. The separation channel, sample aperture, injection aperture and waste aperture may be of various shapes such as, but not limited to, a circular, oval, semi-circular, semi-oval, triangular, rectangular, square or other cross-sectional shapes. In a non-limiting example embodiment, the separation channel has a length of 2 cm and a diameter of 10-100 microns, the sample aperture and the waste aperture has height of 500 microns and a diameter of 1 millimeter and the injection aperture has a height of 500 microns and a diameter of 10-100 microns. The volume of the sample injected into the separation channel is determined by the length of the injection aperture.

Well plate 12 includes sample well 30, buffer well 32 and waste well 34. The sample well, buffer well and waste well may be cylindrically or conically shaped. In a non-limiting example embodiment, bottom plate 14 has a thickness of 1 mm, and well plate 12 has a thickness of 3 mm. In another example embodiment, sample well 30, buffer well 32 (at the central bore) and waste well 34 have a diameter of 2 mm, and buffer well has a diameter of 4 mm.

Bottom plate 14 and well plate 12 are mechanically attached to one another and are secured together by mechanical means (not shown). The mechanical means is also configured to release the bottom plate and well plate when required.

Filter 16 is disposed between the bottom plate 14 and well plate 12. Filter 16, is adjacent to and extends vertically above injection aperture 24. Further, the filter is axially aligned with injection aperture 24 and buffer well 32.

In one embodiment, filter 16 is a compressible membrane that comprises a central portion 16A and a peripheral portion 16B. Central portion 16A is disposed between bottom plate 14 and well plate 12, and is uncompressed. Peripheral portion 16B is adjacent to and surrounds central portion 16A. In a specific embodiment, filter 16 has an uncompressed thickness (at central portion 16A) of 200 microns, a compressed thickness (at peripheral portion 16B) of 160 microns and a diameter of 4 mm. Central portion 16A provides filtration for fluid flow between injection aperture 24 and buffer well 32. Peripheral portion 16B provides a seal between bottom plate 14 and well plate 12 at buffer well 32.

Separation channel 20 is an elongated capillary that extends longitudinally across the microfluidic device 10. Sample aperture 22 is adjacent to and extends vertically above an inlet end of separation channel 20. Injection aperture 24 is adjacent to and extends vertically above separation channel 20 and is downstream (toward the right of the figures) of sample aperture 22. Waste aperture 26 is adjacent to and extends vertically above an outlet end of separation channel 20 and is downstream of injection aperture 24. Detection zone 36 is downstream of injection aperture 24 and upstream of waste aperture 26.

Sample well 30 is adjacent to and extends vertically above and is axially aligned with sample aperture 22. Buffer well 32 is adjacent to and extends vertically above and is axially aligned with injection aperture 24. Waste well 34 is adjacent to and extends vertically above and is axially aligned with waste aperture 26.

In one embodiment, separation channel 20 has a cross-sectional area that is substantially equal to that of injection aperture 24. Sample aperture 22 and waste aperture 26 have cross-sectional areas that are substantially equal. In one embodiment, the cross section of the sample aperture and the waste aperture are substantially larger than that of separation channel 20 and injection aperture 24. Sample well 30, buffer well 32 (at the central bore) and waste well 34 have cross-sectional areas that are substantially equal. The cross-sectional areas are perpendicular to the direction of fluid flow.

Bottom plate 14 and well plate 12 can be formed using a wide variety of materials such as glass, silicon, fused silica, polymer and plastic and can be rigid or flexible. Suitable polymers include polyimide, polycarbonate, polymethyl methacrylate (PMMA), Cyclo olefin copolymer (COC), polydimethylsiloxane (PDMS) and parylene. Filter 16 can be formed using polymers such as cellulose, polyethersulfone, and polycarbonate.

Various fabrication techniques can be applied to form the bottom plate and well plate. Suitable fabrication techniques include photolithography, wet chemical etching, plasma etching, laser drilling, ultrasonic drilling, media blasting, electroforming, printing, stamping, molding, casting, machining, engraving and embossing.

For example, separation channel 20 can be formed as a groove in a cover plate by hot embossing, and sample aperture 22, injection aperture 24 and waste aperture 26 can be formed as through-holes in the cover plate by laser drilling. Thereafter, the cover plate can be attached to a substrate by thermofusion or ultrasonic bonding to seal separation channel 20 so that the substrate forms the lower boundary of separation channel 20. The cover plate and the substrate are integral with one another. In one embodiment, the cover plate, the top plate 13 and bottom plate 14 forms a single-piece unitary structure.

Sample well 30 and waste well 34 can be formed in well plate 12 by laser drilling, and buffer well 32 can be formed in well plate 12 by a combination of laser drilling (to form the central bore) and plasma etching (to form the flanged annular recess). In one embodiment, filter 16 is formed by cutting or slicing a membrane sheet.

Microfluidic device 10 can be assembled by inserting filter 16 into buffer well 32, then positioning bottom plate 14 and well plate 12 such that sample aperture 22, injection aperture 24 and waste aperture 26 are axially aligned with sample well 30, buffer well 32 and waste well 34, respectively, contacting bottom plate 14 and well plate 12 such that sample aperture 22, injection aperture 24 and waste aperture 26 are adjacent to sample well 30, buffer well 32 and waste well 34, respectively, and filter 16 contacts and is sandwiched and compressed between bottom plate 14 and well plate 12, and maintaining secure releasable mechanical attachment between bottom plate 14 and well plate 12, between bottom plate 14 and filter 16 and between well plate 12 and filter 16 using a mechanical means.

Microfluidic device 10 can be repaired or periodically serviced by detaching the bottom plate 14 and well plate 12 by mechanical means, removing filter 16 from buffer well 32, inserting a replacement filter 16 into buffer well 32, and then mechanically reattaching bottom plate 14 and well plate 12. Thus, bottom plate 14 and well plate 12 can be reused and filter 16 can be discarded and replaced.

Bottom plate 14 can also be permanently attached to well plate 12, for instance by glue, epoxy or a thermal bond. Likewise, filter 16 can be permanently attached to bottom plate 14 and/or well plate 12, for instance by glue, epoxy or a thermal bond.

Figure 3A:
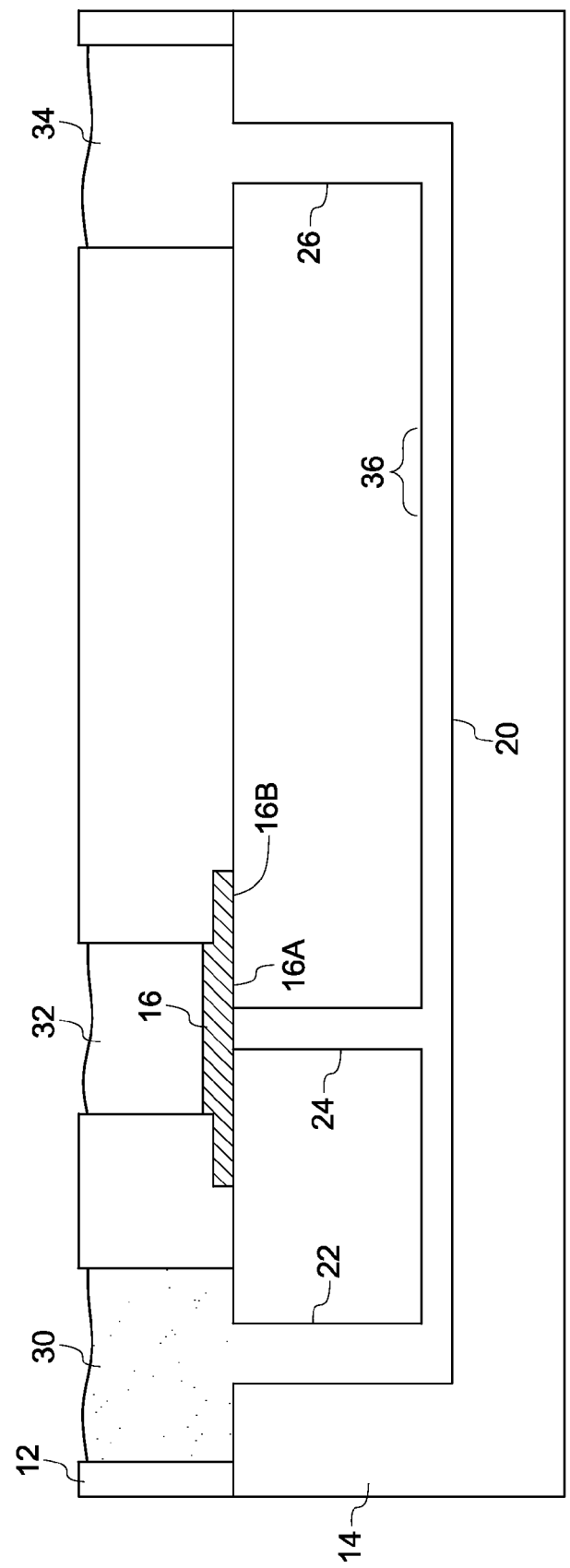
FIG. 3A is a sectional view of a microfluidic device during a load operation.

FIG. 3A is a sectional view of a microfluidic device during a load operation. A separation medium is loaded into separation channel 20, sample aperture 22, injection aperture 24 and waste aperture 26 via sample well 30 or waste well 34 by pressure injection. A buffer is loaded into buffer well 32 and waste well 34 by a syringe or capillary tube. The buffer also includes an electrolyte.

Similarly, a sample is loaded into sample well 30 by a syringe or capillary tube. The separation medium and the buffer are not shown (other than the buffer surface), and the sample is depicted by sparse dots. The sample includes biological analytes such as proteins, peptides, RNA, and DNA fragments and may also include salts and other low molecular weight components.

In one embodiment, the separation medium comprises an electrolyte and a sieving matrix. The electrolyte is a charge-carrying component that conducts electricity and maintains a defined pH. The sieving matrix separates proteins, peptides, RNA, and DNA fragments having different sizes but identical charge-mass ratios in free solution is typically a polymer solution such as polyacrylamide or its derivatives, poly ethylene oxide, hydroxyethyl cellulose and the like.

A sample electrode extends into sample well 30 and contacts the sample in sample well 30. Similarly, a buffer electrode extends into buffer well 32 and contacts the buffer in buffer well 32 and a waste electrode extends into waste well 34 and contacts the buffer in waste well 34. The sample electrode, the buffer electrode and the waste electrode are conductive metals or polymers that are incorporated into or externally applied to microfluidic device 10. Furthermore, the sample electrode, the buffer electrode and the waste electrode (not shown) are connected to a voltage control unit (not shown).

Figure 3B:
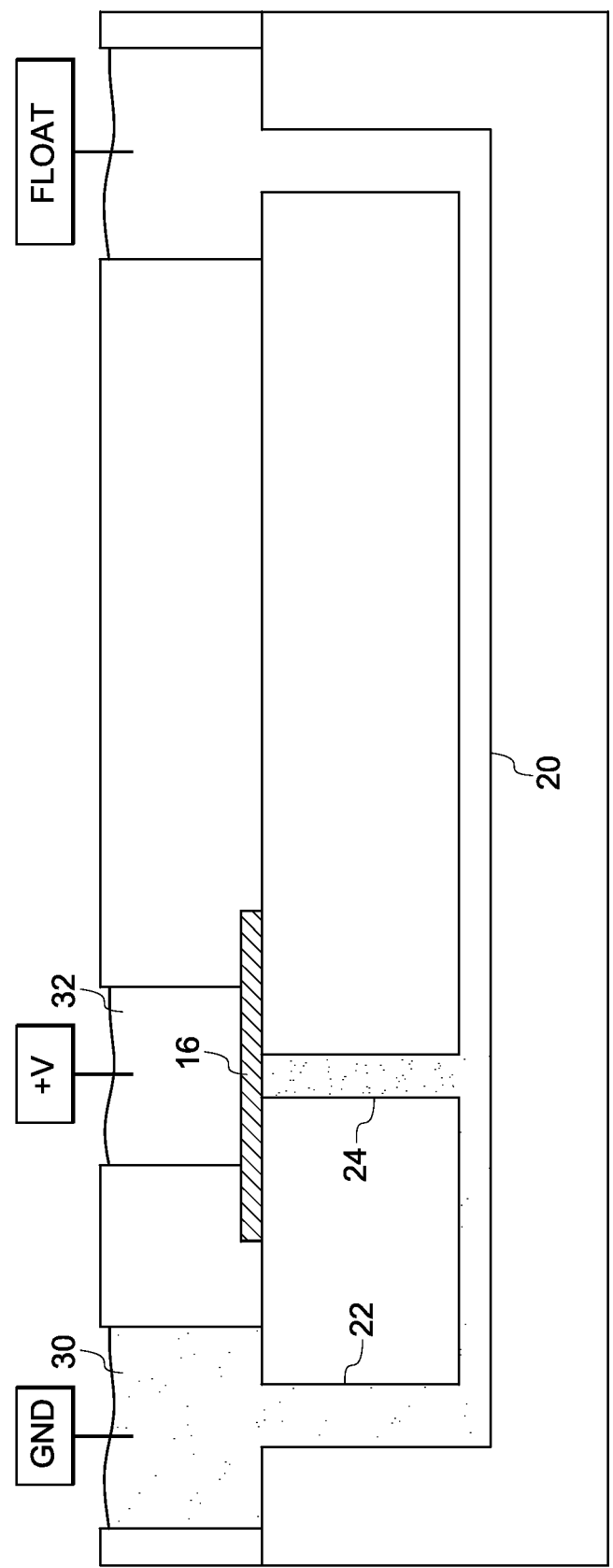
FIG. 3B is a sectional view of a microfluidic device during an injection operation.

FIG. 3B is a sectional view of a microfluidic device during an injection operation. The buffer electrode is switched to positive potential, the sample electrode is switched to negative potential (such as ground), and the waste electrode is allowed to float. The buffer electrode and the sample electrode are configured to create a high intensity electric field that extends from sample well 30 to buffer well 32. In one embodiment, the electric field is 500 volts/cm. The electric field causes the sample to electrokinetically migrate. As a result, the sample flows downwardly from sample well 30 through sample aperture 22 to separation channel 20, flows longitudinally in separation channel 20 downstream to injection aperture 24, and flows upwardly in injection aperture 24 to buffer well 32. However, the sample does not flow longitudinally in separation channel 20 downstream of injection aperture 24.

The sample encounters filter 16 upon reaching buffer well 32. Filter 16 is a semi-permeable membrane that has high hydrodynamic resistance to proteins, peptides, RNA and DNA fragments in the sample and low hydrodynamic resistance to salts and other low molecular weight species in the sample. As a result, the sample concentration is enhanced and salts and other low molecular weight species are removed in the injection aperture 24. A preconcentrated sample plug is formed in injection aperture 24 as the proteins, peptides, RNA, and DNA fragments are blocked by filter 16 and stack in injection aperture 24, and the salts pass through filter 16 and disperse into the buffer in buffer well 32. The sample plug is defined by injection aperture 24 and has tightly controlled volume, size and shape. The sample plug is depicted by dense dots.

Figure 3C:
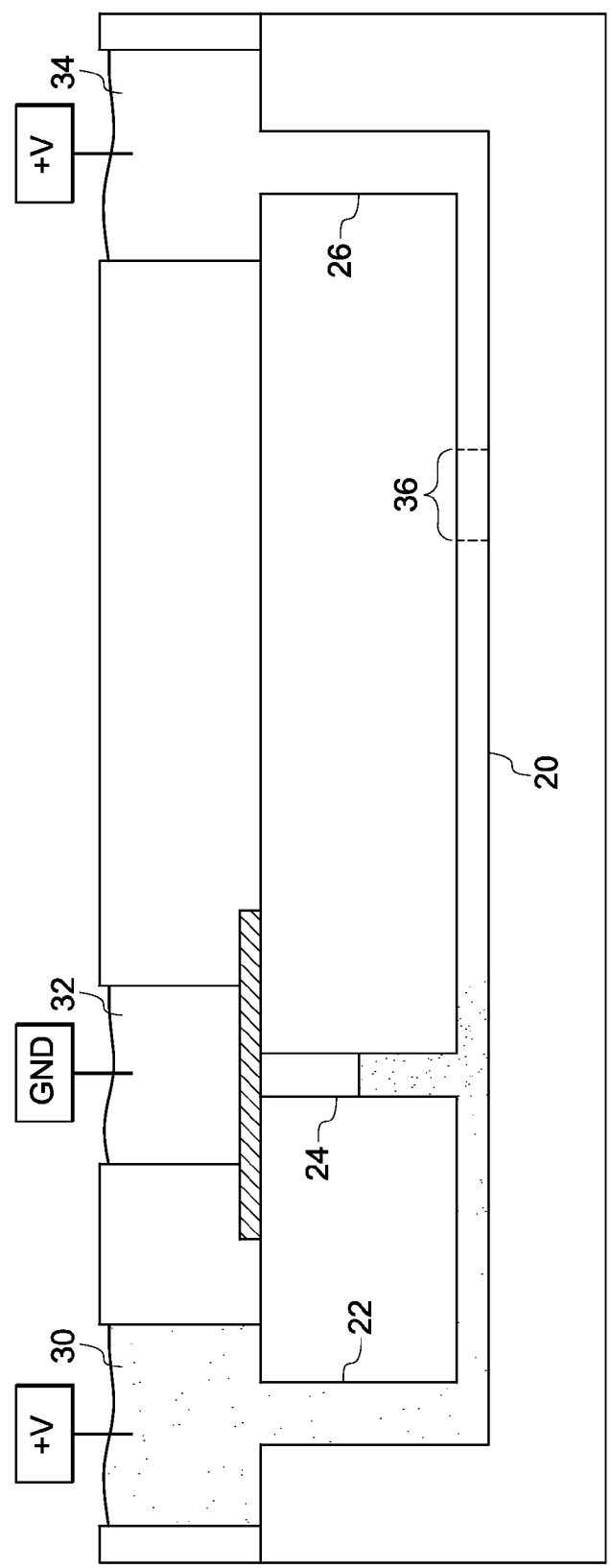
FIG. 3C and FIG. 3D are sectional views of a microfluidic device during an injection operation and during electrophoresis operations.
Figure 3D:
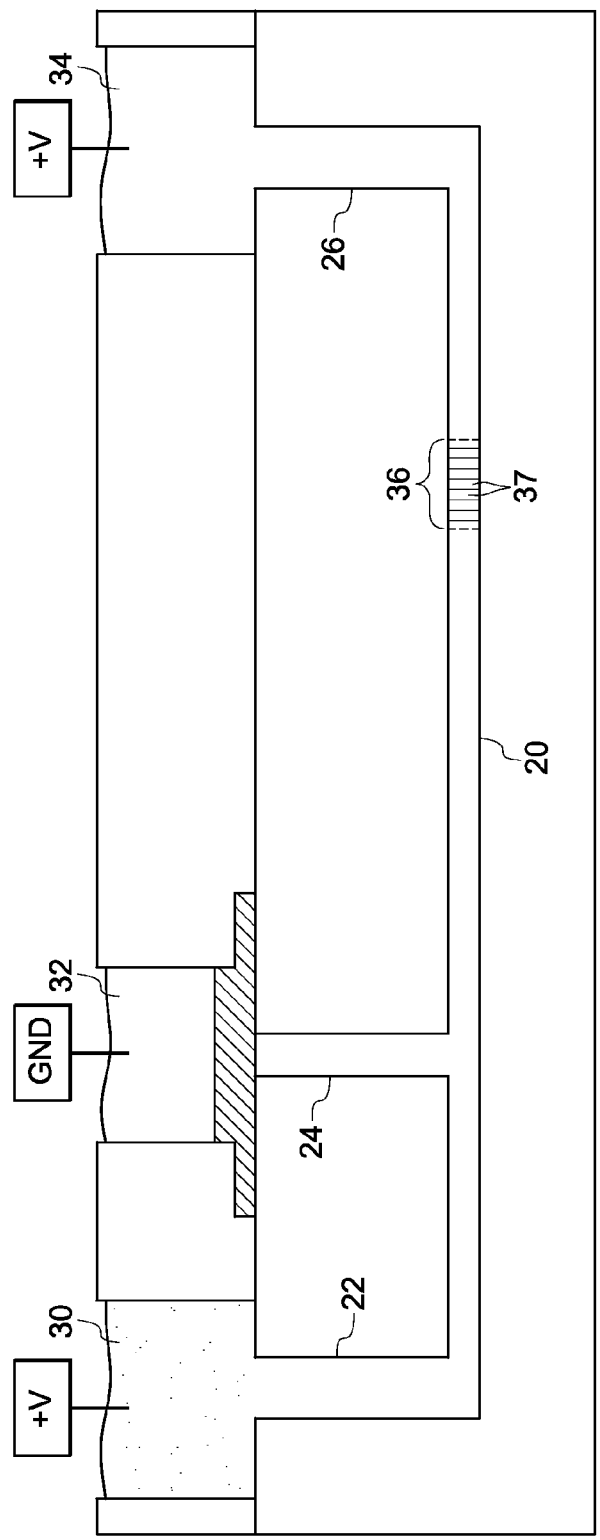

FIGS. 3C and 3D are sectional views of the microfluidic device during an electrophoresis operation. The sample and waste electrodes are switched to positive potential, and the buffer electrode is switched to negative potential (such as ground). The sample electrode, the buffer electrode and the waste electrode create a high intensity electric field that extends from buffer well 32 to sample well 30 and to waste well 34. The electric field causes the sample and the sample plug to electrokinetically migrate.

As a result, the sample in separation channel 20 is pushed back and flows longitudinally in separation channel 20 upstream to sample aperture 22, and flows upwardly in sample aperture 22 to sample well 30. In addition, the sample plug in injection aperture 24 flows downwardly from injection aperture 24 to separation channel 20, then flows longitudinally in separation channel 20 downstream through the separation medium across detection zone 36 to waste aperture 26, and flows upwardly in waste aperture 26 to waste well 34. Furthermore, the sample plug maintains the tightly controlled volume, size and shape defined by injection aperture 24 as it flows through separation channel 20 across detection zone 36.

Although a small portion (about 10 percent) of the sample plug splits off from the main portion at the intersection of separation channel 20 and injection aperture 24 and is pushed back to flow longitudinally in separation channel 20 upstream to sample aperture 22, and flow upwardly in sample aperture 22 to sample well 30, it has no appreciable effect on the electrophoresis operation.

As the sample plug flows longitudinally in separation channel 20 downstream of injection aperture 24, the sample plug electrophoretically separates into bands of molecules having similar electrophoretic mobility. The bands 37 are detected in detection zone 36.

In one embodiment, the bands are detected by an optical detector (not shown). The optical detector can be used to detect the local change in refractive index, absorbance, laser-induced fluorescence, or any other ultraviolet or visible light emission from the bands. In one embodiment, the optical detector is a CCD camera coupled to a computer to generate an electropherogram. Likewise, the bands can be illuminated by a suitable light source (not shown) such as a mercury lamp, an argon ion laser, a solid-state laser and the like. The bands can also be detected using an electrochemical sensor, a pH sensor, a conductivity sensor and/or a thermal sensor.

Figure 4:
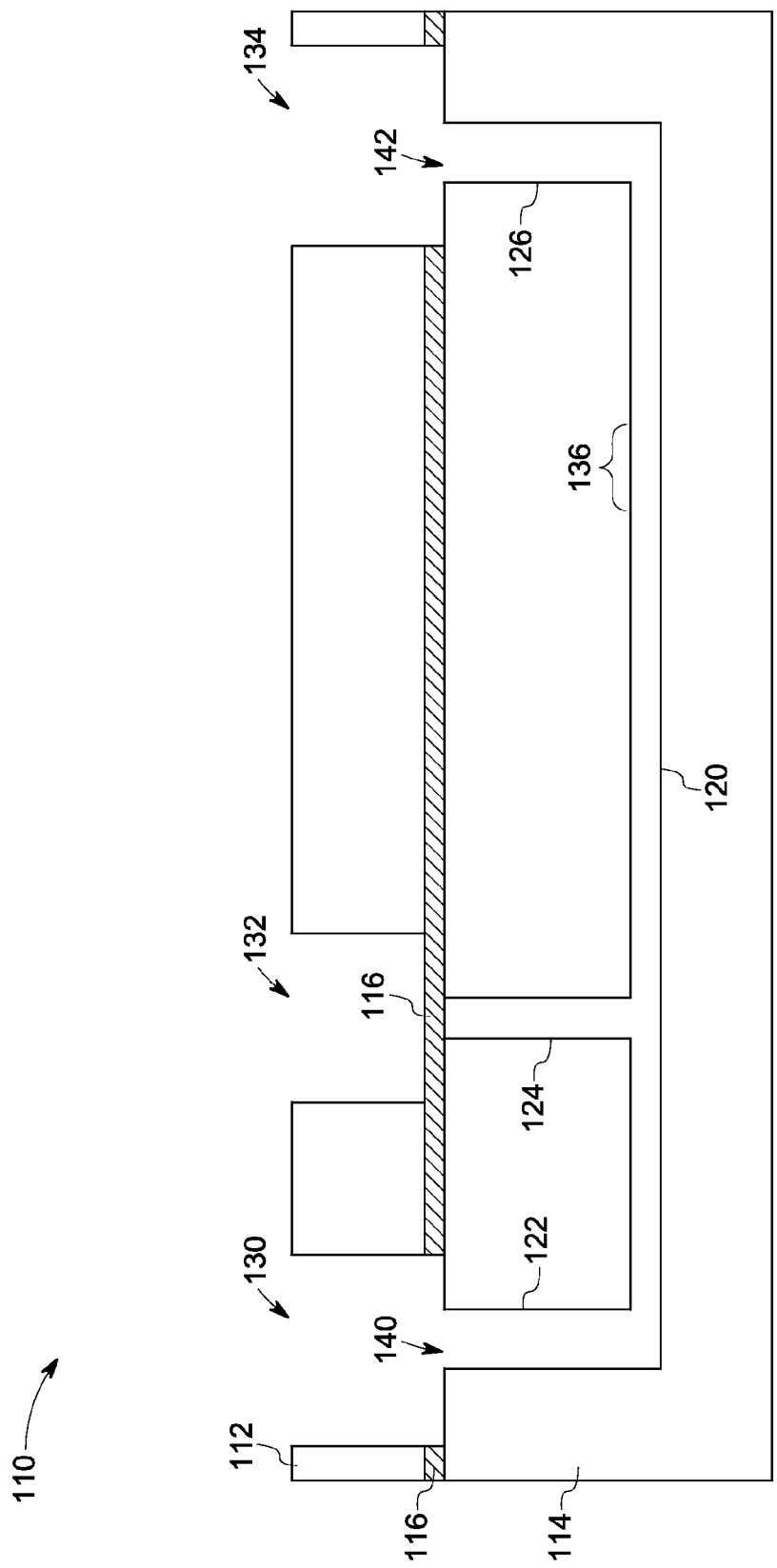
FIG. 4 is a sectional view of another embodiment of a microfluidic device implemented according to one aspect of the invention.
Figure 5:
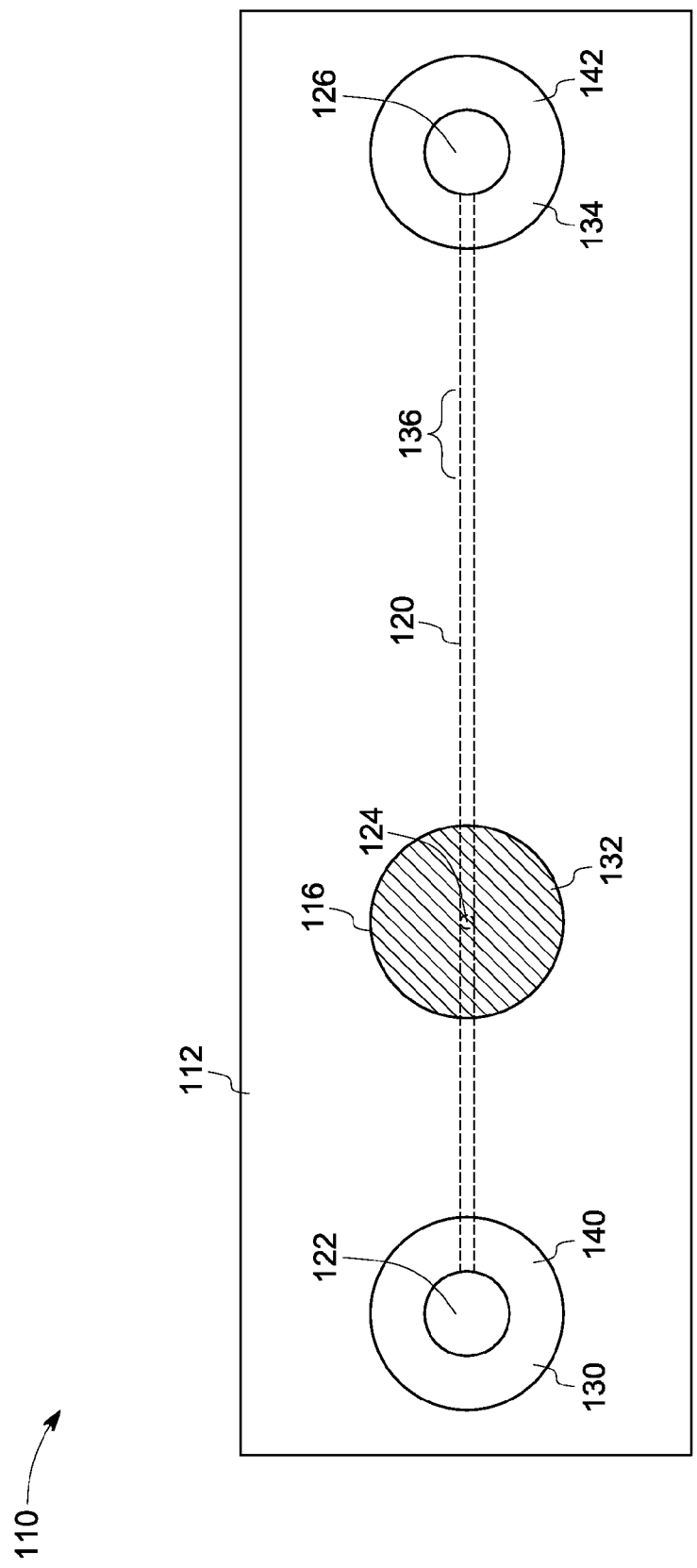
FIG. 5 is a top view of the microfluidic device illustrated in FIG. 4.

FIG. 4 and FIG. 5 are sectional and top plan views, respectively, of microfluidic device 110 in accordance with a second embodiment of the invention. Microfluidic device 110 includes bottom plate 114, well plate 112 and filter 116. Bottom plate 114 includes separation channel 120, sample aperture 122, injection aperture 124 and waste aperture 126. Well plate 112 includes sample well 130, buffer well 132 and waste well 134. Separation channel 120 includes detection zone 136.

Bottom plate 114 is identical to bottom plate 14, and thus separation channel 120, sample aperture 122, injection aperture 124 and waste aperture 126 are identical to separation channel 20, sample aperture 22, injection aperture 24 and waste aperture 26, respectively.

Well plate 112 is identical to well plate 12, except that buffer well 132 is just a central bore and is thus identical to sample well 130 and waste well 134 and devoid of a flanged annular recess.

Filter 116 like filter 16 can be a semi-permeable filter that has high hydrodynamic resistance to proteins, peptides, RNA, and DNA fragments in the sample and low hydrodynamic resistance to salts in the sample. Filter 116 can be polycarbonate, cellulose, or another material used in filtration. Furthermore, filter 116 contacts and is sandwiched between and is releasably secured to bottom plate 114 and well plate 112 and covers and is adjacent to and extends vertically above injection aperture 124. As a result, the sample preconcentrates and desalts and forms a preconcentrated sample plug in injection aperture 124 in the same manner as in injection aperture 24 during the injection operation.

Filter 116 is a stiff layer that is coextensive with and separates bottom plate 114 and well plate 112. Furthermore, filter 116 includes sample hole 140 and waste hole 142. Sample hole 140 is adjacent to and disposed between and in fluid communication with sample aperture 122 and sample well 130. Waste hole 142 is adjacent to and disposed between and in fluid communication with waste aperture 126 and waste well 134. As a result, bottom plate 114 and well plate 112 are spaced from one another, and likewise, sample aperture 122, injection aperture 124 and waste aperture 126 are spaced from sample well 130, buffer well 132 and waste well 134, respectively.

The microfluidic device can include multiple channel and well structures to provide simultaneous injection and electrophoresis operations for multiple samples. In one embodiment, the microfluidic device comprises 96 separation channels that are symmetric and parallel and provide identical separation conditions. The microfluidic device further includes a temperature control unit for controlling the temperature of the separation channel. The microfluidic device also includes chemical coatings in the channels to alter the surface charges.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A microfluidic device, comprising:
a separation channel comprising a detection zone; wherein the detection zone is disposed downstream of an injection aperture and upstream of a waste aperture;
a semi-permeable filter disposed adjacent to and covering the injection aperture, and configured to preconcentrate and desalt a sample to form a preconcentrated sample plug in the injection aperture during an injection operation;
wherein the sample flows downwardly from a sample well through a sample aperture to the separation channel, flows longitudinally in the separation channel from the sample aperture to the injection aperture and flows upwardly in the injection aperture to the filter, and
wherein the sample plug flows downwardly from the injection aperture to the separation channel and flows longitudinally in the separation channel from the injection aperture to the detection zone during an electrophoresis operation;
wherein the separation channel, the sample aperture, the injection aperture and the waste aperture are formed in a bottom plate, the sample well, the buffer well and the waste well are formed in a well plate, and the filter contacts is disposed between the bottom plate and the well plate;
wherein the filter comprises a compressible membrane extending within the buffer well and spaced from the sample well and the waste well; and
wherein the filter further comprises
a central portion covering the injection aperture and contacting the bottom plate and is uncompressed, and
a peripheral portion disposed adjacent to and surrounding the central portion; wherein the peripheral portion is compressed between the bottom plate and the well plate.

2. The microfluidic device of claim 1, wherein the sample aperture is disposed adjacent to the sample well, the injection aperture is disposed adjacent to the buffer well, the waste aperture is disposed adjacent to the waste well and the bottom plate is in contact with the well plate.

3. A microfluidic device, comprising:
a bottom plate comprising a separation channel;
a top plate comprising a sample aperture, an injection aperture and a waste aperture; wherein the sample aperture, the injection aperture and the waste aperture are in fluid communication with the separation channel;
a well plate comprising a sample well, a buffer well and a waste well; and
a semi-permeable filter disposed between the injection aperture and the buffer well.

4. The microfluidic device of claim 3, wherein the bottom plate is formed using at least one of glass, silicon, fused silica, polymer and plastic.

5. The microfluidic device of claim 3, wherein the bottom plate is formed using a first substrate bonded to a second substrate.

6. The microfluidic device of claim 5, wherein the microfluidic device is fabricated using at least one of photolithography, wet chemical etching, plasma etching, laser drilling, ultrasonic drilling, electroforming, printing, stamping, molding, casting, machining, engraving or embossing.

* * * * *